(12) United States Patent
Ditzel et al.

(10) Patent No.: US 7,534,910 B2
(45) Date of Patent: May 19, 2009

(54) PROCESS FOR THE PRODUCTION OF ALKENYL CARBOXYLATES

(75) Inventors: Evert Jan Ditzel, Norh Humberside (GB); Simon Frederick Thomas Froom, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 567 days.

(21) Appl. No.: 10/529,723

(22) PCT Filed: Sep. 29, 2003

(86) PCT No.: PCT/GB03/04220

§ 371 (c)(1),
(2), (4) Date: Mar. 30, 2005

(87) PCT Pub. No.: WO2004/031120

PCT Pub. Date: Apr. 15, 2004

(65) Prior Publication Data

US 2006/0167306 A1    Jul. 27, 2006

(30) Foreign Application Priority Data

Oct. 7, 2002  (GB) ................................. 0223215.5

(51) Int. Cl.
*C07C 67/04* (2006.01)

(52) U.S. Cl. ....................................................... 560/241
(58) Field of Classification Search .................. 560/241
See application file for complete search history.

(56) References Cited

U.S. PATENT DOCUMENTS 6,258,978 B1 *   7/2001   Kitchen et al. .............. 560/248

FOREIGN PATENT DOCUMENTS

| EP | 0 685 449 A1 | 12/1995 |
| EP | 1 006 100 A1 | 6/2000 |

* cited by examiner

*Primary Examiner*—Paul A Zucker
(74) *Attorney, Agent, or Firm*—Nixon & Vanderhye

(57) ABSTRACT

The present invention provides a process for the production of an alkenyl carboxylate by reacting an alkene, a carboxylic acid and a molecular oxygen-containing gas in a reaction zone in the presence of a catalyst at an elevated reaction temperature, T, to produce an outlet stream from the reaction zone comprising alkenyl carboxylate and oxygen, and wherein in said process the catalyst is contacted with the alkene, at a partial pressure, P, optionally in the presence of the carboxylic acid, and the outlet stream comprises less than 2 vol % oxygen, the improvement comprises reducing the partial pressure of the alkene and/or reducing the reaction temperature so as to suppress formation of benzene and/or suppress inhibition of the catalyst.

19 Claims, 3 Drawing Sheets

PROCESS FOR THE PRODUCTION OF ALKENYL CARBOXYLATES

This application is the U.S. National Phase of International Application PCT/GB2003/004220, filed 29 Sep. 2003, which designated the U.S. PCT/GB2003/004220 claims priority to British Application No. 0223215.5 filed 7 Oct. 2002. The entire content of these applications are incorporated herein by reference.

The present invention relates to a process for the production of alkenyl carboxylates, and, in particular to a process for the production of vinyl acetate.

Vinyl acetate is generally prepared commercially by contacting ethylene and acetic acid with molecular oxygen in the presence of a catalyst active for the production of vinyl acetate. The process may be carried out in either a fixed bed or a fluid bed reactor. A process employing a fixed catalyst bed is described, for example, in EP-A-0845453. Processes employing a fluidised catalyst bed are described, for example, in EP-A-0672453, EP-A-0685449, EP-A-0685451, EP-A-0985655 and EP-A-1008385. For example, EP-A-0 672 453 describes a process for the fluid bed production of vinyl acetate from ethylene, acetic acid and a molecular oxygen-containing gas in the presence of a promoted palladium catalyst.

Catalysts active for the production of vinyl acetate may typically comprise a Group VIII metal, such as palladium; a co-promoter, such as gold, copper, cerium or mixtures thereof; and, optionally, a co-promoter, such as potassium acetate. For example, catalysts active for the production of vinyl acetate are described in GB 1 559 540; U.S. Pat. No. 5,185,308 and EP-A-0672453 the contents of which are hereby incorporated by reference. EP-A-0672453, for example, describes palladium containing catalysts and their preparation for fluid bed vinyl acetate processes.

A commercial vinyl acetate process is generally operated as a continuous process. Ideally, the vinyl acetate process is started up smoothly. However, numerous problems (process upsets) can occur during both the start-up and operation of the process. In addition to any process upsets, a commercial vinyl acetate process also has planned shut-downs, for example, for the periodic maintenance of the plant and/or replacement of deactivated catalyst with fresh catalyst.

When a process upset occurs in the production of vinyl acetate from ethylene, acetic acid and molecular oxygen, the molecular oxygen-containing gas feed to the reaction zone is usually shut-off. In addition, it may or may not also be desirable to shut off the acetic acid feed to the reaction zone. Irrespective of whether or not the acetic acid feed is shut-off, the catalyst will be exposed to ethylene in the substantial absence of molecular oxygen. Typically, during a planned shut-down, the molecular oxygen-containing gas feed to the reaction zone is shut-off prior to shutting-off the acetic acid feed. The catalyst will then be left exposed to ethylene in the substantial absence of molecular oxygen.

It has been found that where catalysts suitable for use in the production of alkenyl carboxylates, such as vinyl acetate, are exposed to alkene in the absence or substantial absence of molecular oxygen the catalyst shows unexpectedly low activity on starting-up or restarting of the process. Due to this unexpected loss in catalytic activity (catalyst inhibition), the production rate is low and significantly lower than expected.

Furthermore, as a result of this reduction in catalytic activity, molecular oxygen introduced in to the reactor on starting-up or restarting the process may not be consumed thereby creating an accumulation of unreacted molecular oxygen in the reactor and increasing the risk of explosion.

In addition, it has also been found that where alkenyl carboxylate catalysts are exposed to an alkene, optionally in the presence of a carboxylic acid, at relatively low levels of molecular oxygen, benzene production may occur. Benzene has a similar boiling point to vinyl acetate and therefore separation of the two components is difficult to achieve. Undesirably, therefore, the vinyl acetate product may contain unacceptable levels of benzene. It is therefore desirable to reduce or eliminate the formation of benzene in the production of vinyl acetate. In particular, it is desirable to produce a vinyl acetate product comprising less than 100 ppb benzene.

Thus, there remains a need for an improved process for the production of alkenyl carboxylates, such as vinyl acetate. In particular, there is a need for a process in which catalyst inhibition and/or benzene formation are suppressed.

Thus, according to the present invention there is provided a process for the production of an alkenyl carboxylate by reacting an alkene, a carboxylic acid and a molecular oxygen-containing gas in a reaction zone in the presence of a catalyst at an elevated reaction temperature, T, to produce an outlet stream from the reaction zone comprising alkenyl carboxylate and oxygen, and wherein in said process the catalyst is contacted with the alkene, at a partial pressure, P, optionally in the presence of the carboxylic acid, and the outlet stream comprises less than 2 vol % oxygen, the improvement comprises reducing the partial pressure of the alkene and/or reducing the reaction temperature so as to suppress formation of benzene and/or suppress inhibition of the catalyst.

Typically, the partial pressure of alkene, P, such as ethylene, in the reaction zone is at least 0.3 bar or greater, such as at least 1 bar, for example, at least 2 bar.

The partial pressure of alkene in the reaction zone is suitably reduced to at least 50% less than P. Typically, P is at least 2 bar, and the partial pressure of alkene in the reaction zone is reduced to less than 1 bar. Preferably, the partial pressure of alkene in the reaction zone is reduced to approximately 0 bar by removing substantially all the alkene from the reaction zone when low levels of molecular oxygen are present. In one embodiment of the present invention, reducing the partial pressure of alkene comprises removing all reactant gases (i.e. alkene, optional carboxylic acid, and any oxygen present) from the reaction zone, for example by purging the reaction zone with an inert gas, such as nitrogen.

The reaction is typically carried out at a temperature, T, of at least 100° C., such as at least 140° C.

The reaction temperature is preferably reduced to at least 20° C. below T, such as to at least 50° C. below T. More preferably, the reaction temperature is reduced to below 100° C., such as to 50° C. or lower, for example, to ambient temperature, such as approximately 20° C.

Generally, in the manufacture of an alkenyl carboxylate, such as vinyl acetate, operating at steady-state conditions, the concentration of oxygen in the outlet stream from the reaction zone is greater than 2 vol %. However, during start-up, shut-down or process upsets the concentration of oxygen in the outlet stream may be at a low level, that is less than 2 vol %, such as 0 to 0.5 vol % or 0 to 0.2 vol %.

In general, the amount of benzene produced on exposure of the catalyst to the alkene in the presence of low levels of oxygen will vary, depending on, for example, the exact oxygen concentration in the outlet stream, the reaction temperature, the specific catalyst used, the alkene partial pressure and the total reaction pressure. In addition, the amount of benzene produced will depend on the period of time for which the catalyst is exposed to the alkene in the presence of low levels of oxygen.

In the present invention, the catalyst will be exposed to an alkene (and optionally carboxylic acid) in the presence of low levels of oxygen for a period of time (period of contact), Z, before the partial pressure of the alkene and/or the reaction temperature are reduced. Generally, the period of contact, Z, should be minimized.

For example, where the catalyst is exposed to alkene at low levels of oxygen for short periods of time at relatively low reaction temperatures, only relatively small amounts of benzene may be produced which do not significantly affect product quality.

However, higher amounts of benzene may be expected to be produced where the oxygen concentration in the outlet stream is significantly lower than 2 vol %, such as 0 to 0.5 vol %, and/or where the catalyst is exposed to alkene at low levels of oxygen for longer periods of time.

Benzene formation may be determined by any suitable method known in the art, for example, such as gas chromatography and/or mass spectrometry. The amount of benzene produced may be measured, for example, in the outlet stream directly at the outlet of the reaction zone and/or at a point downstream of the outlet from the reaction zone, such as in the final vinyl acetate product.

It has also been found that if the oxygen concentration in the outlet stream is reduced significantly below 2 vol %, such as to 0.5 vol % or less, the catalyst becomes inhibited. Catalyst employed in a process for the production of alkenyl carboxylate prior to a shut-down or a process upset will have become inhibited if it shows more than a 10% loss in activity on resumption of normal operating conditions of the process compared to its activity immediately prior to the shut-down/process upset.

It has been found that the extent to which the catalyst becomes inhibited is dependent on the time (period of contact) over which the catalyst is exposed to alkene, and optionally carboxylic acid, in the substantial absence of oxygen.

The activity of a catalyst may be determined by any suitable method known in the art, for example, by analysis of the amount of product produced using a suitable analytical techniques, such as gas chromatography and/or mass spectrometry. Typically, in a fluid bed process for the manufacture of vinyl acetate, the production rate of vinyl acetate is suitably determined by calculating the amount of vinyl acetate product produced per unit catalyst per unit time. For example, the space-time yield may be measured as the production of vinyl acetate in grammes of vinyl acetate produced per kilogram of catalyst per hour (gVA/kg-cat/hr).

The present invention also provides a process for the production of an alkenyl carboxylate in which an alkene, a carboxylic acid and a molecular oxygen-containing gas are contacted in a reaction zone at an elevated temperature, T, in the presence of a catalyst having a catalytic activity y, comprising a Group VIII metal, a promoter and an optional co-promoter, characterised in that where during the course of said process, the catalyst is contacted with the alkene, optionally in the presence of the carboxylic acid, and in the substantial absence of the molecular oxygen-containing gas, the period of contact, Z, between the catalyst and the alkene, and optional carboxylic acid is insufficient to reduce the catalytic activity by more than 10% of y.

In a preferred embodiment of the process of the present invention, the alkenyl carboxylate is vinyl acetate. Thus, the present invention accordingly provides a process for the production of vinyl acetate in which ethylene, acetic acid and a molecular oxygen-containing gas are contacted in a reaction zone at an elevated temperature, T, in the presence of a catalyst having a catalytic activity y, comprising a Group VIII metal, a promoter and an optional co-promoter, characterised in that where during the course of said process, the catalyst is contacted with ethylene, optionally in the presence of acetic acid, in the substantial absence of the molecular oxygen-containing gas, the period of contact between the catalyst and ethylene, and optional acetic acid is insufficient to reduce the catalytic activity by more than 10% of y.

The exact degree of inhibition of the catalyst may also be dependent upon factors other than the oxygen concentration and the period of contact, Z, such as the specific nature of the catalyst employed, the sensitivity of the catalyst to the alkene and carboxylic acid, the nature of the reactant(s) to which the catalyst is exposed and their partial pressures, and also the reaction temperature. Generally, however, the period of contact, Z, between the catalyst and alkene (and optionally carboxylic acid) in the substantial absence of oxygen should be minimized. Suitably, in the production of vinyl acetate using a promoted Group VIII metal, such as palladium, the period of contact, Z, of the catalyst with ethylene or ethylene and acetic acid, in the substantial absence of molecular oxygen, is in the range [>0 to 18] hours, preferably, in the range, [>0 to 12] hours and more preferably, in the range [>0 to 6] hours.

Inhibition of the catalyst may be greater where the catalyst is exposed to both alkene and carboxylic acid, in the substantial absence of molecular oxygen. Thus, where the catalyst is contacted with alkene and carboxylic acid, such as ethylene and acetic acid, in the substantial absence of molecular oxygen, the period of contact is preferably less than the period of contact with alkene alone. Suitably, therefore, the period of contact, Z, is in the range [>0 to 12] hours, preferably, in the range [>0 to 6] hours.

Catalyst inhibition may also be at least partially mitigated by reducing the partial pressure of carboxylic acid in the reaction zone, even if the partial pressure of alkene is not reduced or the reaction temperature is not reduced. Preferably, however, to avoid or mitigate catalyst inhibition and simultaneously to avoid or mitigate benzene production, the partial pressure of alkene is reduced and/or the temperature is reduced.

By minimising the contact time of the catalyst with the alkene or alkene and carboxylic acid, in the substantial absence of molecular oxygen, reduction in catalytic activity can be avoided or at least mitigated thereby avoiding prolonged start-up periods and/or reducing the time taken before the process recovers fill production rates after a shutdown. In particular, fluid bed processes may be run at higher nominal molecular oxygen levels in the reaction zone than in fixed bed processes. Thus, for example, on start-up of a fluid bed process, in which the catalyst is, prior to the introduction of the molecular oxygen-containing gas, contacted with alkene or alkene and carboxylic acid for a prolonged period of time, the catalyst loses activity and therefore the molecular oxygen introduced into the reaction zone is unconsumed, leading to high levels of molecular oxygen in the reaction zone outlet and an increased risk of explosion. By employing the process of the present invention unsafe operation is mitigated.

Unless otherwise stated all measurements of composition by percentage throughout this specification are measurements in terms of percentage by volume. The volume of molecular oxygen in the outlet stream from the reaction zone, as used herein, is measured on a "dry-gas" basis i.e. after removal of condensables that may be present in the outlet stream at the exit of the reaction zone.

Typically, the production of alkenyl carboxylate such as vinyl acetate is carried out heterogeneously with the reactants being present in the gas phase or as a mixture of gas and liquid phases. The process of the present invention may be carried out as a fixed bed or a fluid bed process, preferably, a fluid bed process.

The alkene may be any suitable alkene or a mixture of alkenes, but is preferably a $C_2$-$C_4$ alkene, such as ethylene.

The alkene may be fed in substantially pure form or admixed with other materials, such as, for example, other alkenes or hydrocarbons, hydrogen or inert materials. For example, where the alkene is ethylene, the ethylene may be fed in substantially pure form or may be fed admixed with one or more of nitrogen, methane, ethane, carbon dioxide, water in the form of steam, hydrogen and $C_3$/$C_4$ alkenes or alkanes.

The alkene may comprise fresh and/or recycle alkene.

The fresh and recycle alkene, for example, ethylene, may be introduced into the reaction zone either as separate feed streams or as a single feed stream comprising both fresh and recycle alkene.

The carboxylic acid may be any carboxylic acid or a mixture of carboxylic acids, but is preferably a $C_2$-$C_4$ carboxylic acid, such as acetic acid.

The alkenyl carboxylates that may be produced in the process of the present invention include vinyl propionate, allyl acetate and allyl propionate.

Preferably, however, where the alkene is ethylene, the carboxylic acid used in the process of the present invention is acetic acid, such that the alkenyl carboxylate produced is vinyl acetate.

The carboxylic acid may be introduced into the reaction zone in liquid form or in vapour form. Where the process is a fixed bed process then the carboxylic acid is preferably introduced in to the reaction zone in vapour form. Where the process is a fluid bed process then the carboxylic acid is preferably introduced in to the reaction zone as a liquid spray.

The carboxylic acid may comprise fresh and/or recycle acid.

The fresh and recycle carboxylic acid may be introduced into the reaction zone either as separate feed streams or as a single feed stream comprising both fresh and recycle acid.

The carboxylic acid may comprise at least a portion of the acid obtained from downstream processes such as from the separation of the acid from a mixture of the acid/alkenyl carboxylate/water.

The molecular oxygen-containing gas may be any suitable gas containing molecular oxygen and may suitably be air or a gas richer or poorer in molecular oxygen than air. A suitable molecular oxygen-containing gas may be, for example, oxygen diluted with a suitable diluent, for example nitrogen, argon or carbon dioxide. Preferably, the molecular oxygen-containing gas is essentially pure oxygen.

Under normal operating conditions the alkene, carboxylic acid and molecular oxygen-containing gas may be introduced into the reaction zone in any suitable proportions for the production of the alkenyl carboxylate. For example, the alkene may be present in the feed to the reaction zone in a range between 30 and 85 mol % of the total reaction composition, preferably at least 50 mol %, such as in an amount of at least 60 mol % of the total reaction composition. The carboxylic acid may be present in the feed to the reaction zone in a range between 2 and 30 mol % of the total reaction composition, preferably 5 to 15 mol %. The amount of molecular oxygen-containing gas present in the feed to the reaction zone is controlled by flammability constraints. In a fixed bed reactor the molecular oxygen-containing gas is preferably introduced to the reaction zone via the recycle gas and the feed to the reaction zone must be such that the mixture is non-flammable, for example oxygen may be present in a range 3 to 9 mol % of the total reaction composition. In a fluid bed reactor the molecular oxygen-containing gas is preferably added directly to the reaction zone and the oxygen may be present at a higher level, for example, in a range 3 to 20 mol % of the total reaction composition. A balance of an inert gas, preferably one or more of nitrogen, carbon dioxide and argon may also be present in the reactant feed.

The catalyst for use in the process of the present invention may be any promoted Group VIII metal suitable for the production of an alkenyl carboxylate from an alkene, carboxylic acid and a molecular oxygen-containing gas.

Where vinyl acetate is the alkenyl carboxylate, the catalyst suitable for use in the production of vinyl acetate in a fixed bed process may comprise any suitable catalyst known in the art, for example, as described in GB 1 559 540 and U.S. Pat. No. 5,185,308.

GB 1 559 540 describes a catalyst active for the preparation of vinyl acetate by the reaction of ethylene, acetic acid and molecular oxygen, the catalyst consisting essentially of:

(1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per litre of catalyst, and the gold being present in an amount of from 0.5 to 2.25 grams per litre of catalyst, and (3) from 5 to 60 grams per litre of catalyst of alkali metal acetate.

U.S. Pat. No. 5,185,308 describes a shell impregnated catalyst active for the production of vinyl acetate from ethylene, acetic acid and a molecular oxygen containing gas, the catalyst consisting essentially of:

(1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

A catalyst suitable for use in the production of vinyl acetate in a fluid bed process may comprise a Group VIII metal, a catalyst promoter and an optional co-promoter.

With regards to the Group VIII metal, the preferred metal is palladium. Suitable sources of palladium include palladium (II) chloride, sodium or potassium tetrachloropalladate, (II), ($Na_2PdCl_4$ or $K_2PdCl_4$), palladium acetate, palladium (II) nitrate or palladium (II) sulphate. The metal may be present in a concentration of greater than 0.2% by weight, preferably greater than 0.5% by weight based upon total weight of catalyst. The metal concentration may be as high as 10% by weight. Generally, the higher the active metal loading in a catalyst suitable for use in vinyl acetate production, the more catalytically active it will be. In addition to the Group VIII metal, the catalyst for the production of vinyl acetate comprises a promoter. Suitable promoters include gold, copper, cerium or mixtures thereof. A preferred promoter is gold. Suitable sources of gold include gold chloride, tetrachloroauric acid ($HAuCl_4$), $NaAuCl_4$, $KAuCl_4$, dimethyl gold acetate, barium acetoaurate or gold acetate. The preferred gold compound is $HAuCl_4$. The promoter metal may be present in an amount of from 0.1 to 10% by weight in the finished catalyst.

The catalyst suitable for use in the production of vinyl acetate may also comprise a co-promoter material. Suitable co-promoters include Group I, Group II, lanthanide or transition metals, for example cadmium, barium, potassium, sodium, manganese, antimony, and/or lanthanum, which are present in the finished catalyst as salts, e.g. an acetate salt. The preferred salts are potassium or sodium acetate. The co-promoter is preferably present in the catalyst composition in a concentration of 0.1 to 15% by weight of catalyst, more preferably, from 1 to 5% by weight.

Where a liquid acetic acid feed is used the preferred concentration of co-promoter salt is up to 6% by weight, especially 2.5 to 5.5%. Where the acid is introduced in the vapour phase the co-promoter salt is preferably present in a concentration up to 11 wt %.

The catalyst may be a supported catalyst. Suitable catalyst supports include porous silica, alumina, silica/alumina, titania, silica/titania or zirconia. Where the catalyst is a catalyst suitable for use in the production of vinyl acetate, and in particular for use in a fluid bed process, the support is preferably silica, and, suitably, the support may have a pore volume from 0.2 to 3.5 ml per gram of support, a surface area of 5 to 800 $m^2$ per gram of support and an apparent bulk density of 0.3 to 1.5 g/ml.

In a fluid bed reactor the particles of the catalyst are maintained in a fluidised state by a suitable gas flow through the system. Excess flow rate may cause channeling of the gas through the reactor which decreases conversion efficiency.

A typical catalyst useful in the production of vinyl acetate in a fluidised bed reaction may have the following particle size distribution:

| | | |
|---|---|---|
| 0 to 20 | microns | 0-30 wt % |
| 20 to 44 | microns | 0-60 wt % |
| 44 to 88 | microns | 10-80 wt % |
| 88 to 106 | microns | 0-80 wt % |
| >106 | microns | 0-40 wt % |
| >300 | microns | 0-5 wt % |

Persons skilled in the art will recognize that support particles sizes of 44, 88, 106 and 300 microns are arbitrary measures in that they are based on standard sieve sizes. Particle sizes and particle size distributions may be measured by an automated laser device such as a Microtrac X100.

The catalyst may be prepared by any suitable method. For example the catalyst for the production of vinyl acetate may be prepared by the method detailed in EP-A-0672453, the contents of which are hereby incorporated by reference.

The method of catalyst preparation may be varied to optimise catalyst performance based on maximising yield and selectivity.

The process of the present invention may be carried out at a temperature in the reaction zone, T, from 100 to 400° C. and at atmospheric or at greater than atmospheric pressure, for example, at up to 20 barg.

For example, the process for the production of vinyl acetate when carried out in a fluid bed reaction zone may suitably be operated at a temperature from 100 to 400° C., preferably 140 to 210° C. and a pressure of $1\times10^5$ to $2\times10^6$ Pa gauge (1 to 20 barg), preferably $6\times10^5$ to $1.5\times10^6$ Pa gauge (6 to 15 barg), especially $7\times10^5$ to $1.2\times10^6$ Pa gauge (7 to 12 barg).

The process for the production of vinyl acetate when carried out in a fixed bed reaction zone may suitably be operated at a temperature from 100 to 400° C., preferably 140 to 180° C. and a pressure of $1\times10^5$ to $2\times10^6$ Pa gauge (1 to 20 barg), preferably $6\times10^5$ to $1.5\times10^6$ Pa gauge (6 to 15 barg), especially $7\times10^5$ to $1.2\times10^6$ Pa gauge (7 to 12 barg).

BRIEF DESCRIPTION OF THE DRAWINGS

The invention will now be illustrated by reference to the following Examples and Figures.

EXAMPLES

Example 1

These experiments demonstrate the effect on catalytic activity of:
1) contacting a vinyl acetate catalyst with ethylene prior to contacting with oxygen
2) contacting a vinyl acetate catalyst with a mixture of ethylene and acetic acid prior to contacting with oxygen.

A 1.8 g sample of a promoted palladium vinyl acetate catalyst was mixed with 20-22 g of inert diluent, and contacted for a period of 18, 66 or 138 hours with either ethylene or a mixture of ethylene and acetic acid, at 160° C. and 8 barg in a fluidised bed microreactor.

The flow rates of ethylene and acetic acid were 0.49 mol/hr and 0.05 mol/hr respectively. The fluidised bed microreactor had a diameter of 1" and was fitted with baffle trays. Gas flow was provided through a plenum at the base of the unit, and also from a small sparger mounted within the fluid bed.

After the pre-treatment with ethylene or a mixture of ethylene and acetic acid, each catalyst was tested in the fluidised bed microreactor operated at 160° C./ and 8 bar.

A reaction mixture of 52mol % ethylene, 5 mol % acetic acid and 1.9mol % oxygen, with a nitrogen balance at a total flow rate of 0.93 mol/hr was fed into the reactor. Samples were removed periodically and vinyl acetate was measured by gas chromatography (GC).

Figure 1:
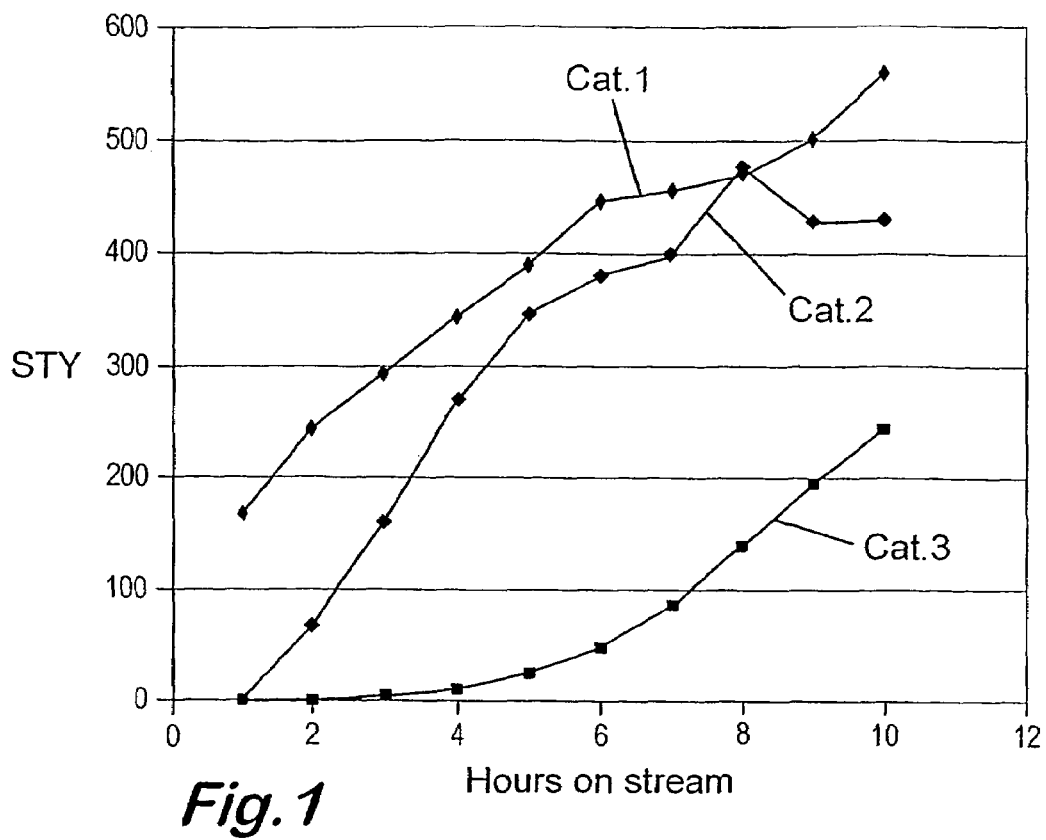
FIG. 1 is a graph illustrating the effect on catalytic activity of pre-treating a vinyl acetate catalyst with ethylene or a mixture of ethylene and acetic acid, prior to contacting with oxygen.
Figure 2:
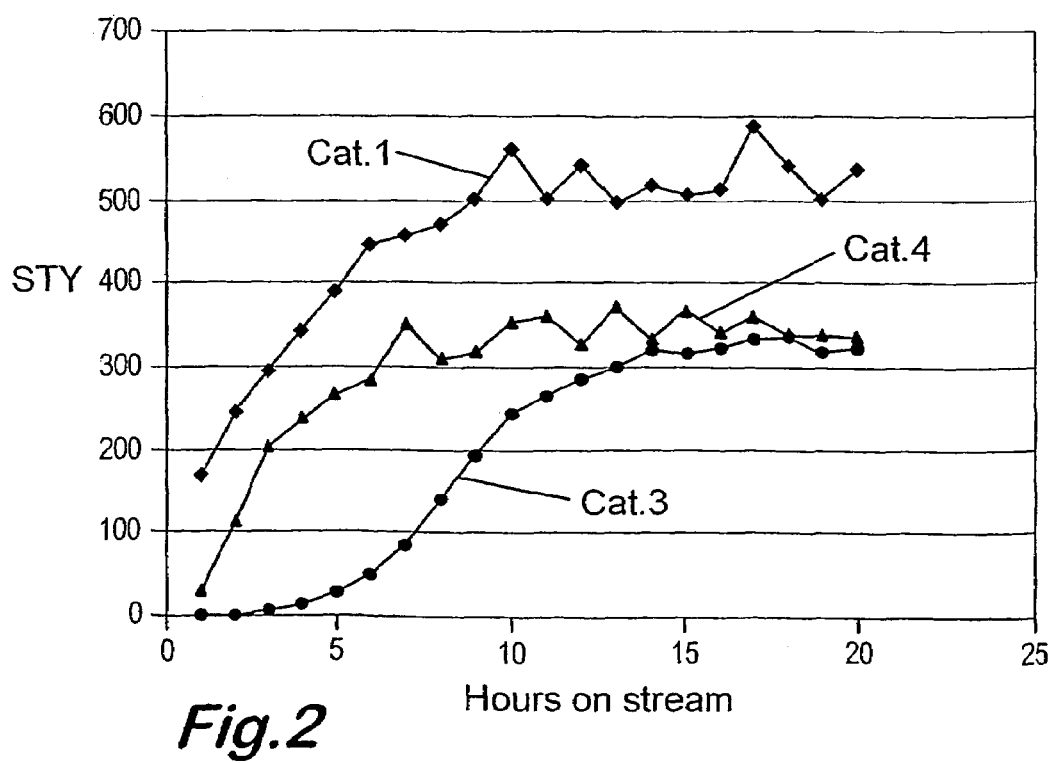
FIG. 2 is a graph illustrating the effect on catalytic activity of pre-treating a vinyl acetate catalyst with a mixture of ethylene and acetic acid, prior to contacting with oxygen.

The results are shown in FIGS. 1 and 2. FIG. 1 shows the activity profile (space time yield (STY) in gVA/Kg-cat/hr) for a fresh, non pre-treated catalyst (catalyst 1) compared to equivalent catalysts (2 and 3) that have been pre-treated by exposure to ethylene and a mixture of ethylene and acetic acid respectively for 138 hours. It can be seen that both catalysts 2 and 3 have a significantly reduced initial activity compared to the non-pretreated catalyst. With time on stream the catalysts start to regain some of the lost activity.

It can also be seen that the catalyst exposed to a mixture of ethylene and acetic acid (catalyst 3) is more severely inhibited than that exposed to ethylene alone (catalyst 2).

FIG. 2 shows a comparison of the non pre-treated catalyst (catalyst 1, as above) with catalysts that have been pre-treated in a mixture of ethylene and acetic acid for two different periods of time, namely 18 hours (catalyst 4) and 138 hours (catalyst 3, as above) respectively.

It can be seen that the initial extent of catalyst inhibition is related to the length of time for which the catalyst was exposed to the mixture of ethylene and acetic acid.

Example 2

300 g samples of promoted palladium vinyl acetate catalysts were pre-treated for 18 hours (unless otherwise stated) in a fluidised bed reactor with a diameter of 1½" (38 mm), fitted with baffle trays with the materials as specified in Table 1. Gas flow was provided through a plenum at the base of the unit, and also from a small sparger mounted within the fluid bed. Heating was provided by a three-zone oil jacket, and the feed gases were pre-heated before entering the reactor. The reactor was operated at 8 barg and 155° C. Nitrogen was used in all pre-treatments unless otherwise stated.

| Catalyst | Pre-treatment atmosphere |
| --- | --- |
| 5 | Ethylene, acetic acid, vinyl acetate, nitrogen |
| 6 | Ethylene, nitrogen (with purge*) |
| 7 | Ethylene, acetic acid, nitrogen |
| 8 | Acetic acid, nitrogen |
| 9 | Ethylene, nitrogen |

*catalyst purged overnight with nitrogen after ethylene/nitrogen pre-treatment but before reaction.

After the pre-treatment the reactor was purged with nitrogen for 1 hour. A feed comprising 60 mol % ethylene, 12 mol % acetic acid, 6.8 mol % oxygen, balance nitrogen was then fed into the reactor. The oxygen flow in to the reactor was recorded in grammes per hour (g/hr) using a mass flow controller. The oxygen level in the stream exiting the reactor was measured using a Servomex oxygen analyser, which reported in weight percent (wt %).

Figure 3:
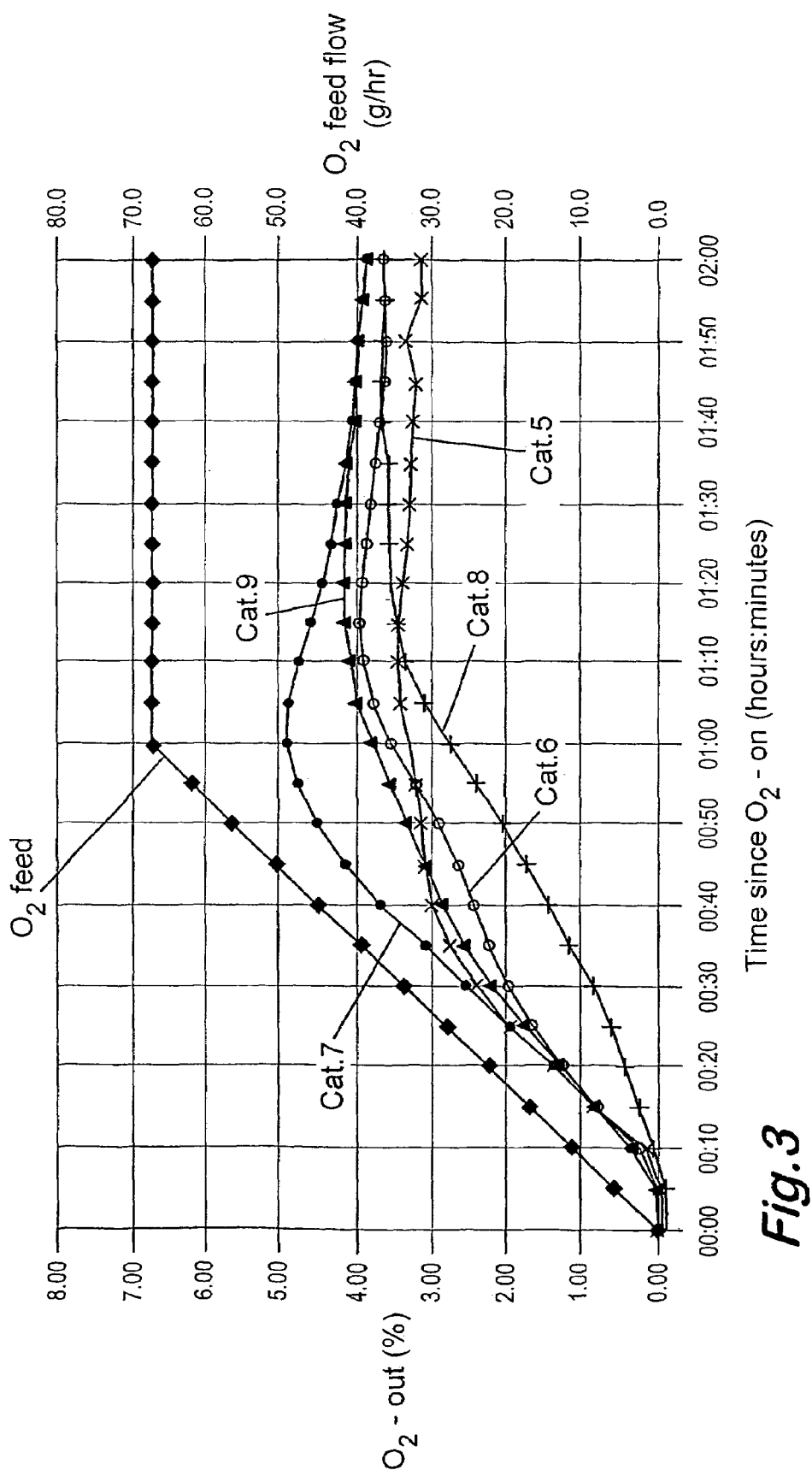
FIG. 3 is a graph illustrating the effect on the oxygen concentration of the product stream from the reaction zone of a vinyl acetate fluidized bed reactor by pre-treating the catalyst with ethylene or a mixture of ethylene and acetic acid.

The results are shown in FIG. 3. FIG. 3 shows the oxygen levels exiting the reactor for pre-treated catalysts 5 to 9 compared to the oxygen level in the feed to the reactor. Varying levels of inhibition can be observed based on the time taken for the oxygen levels in the outlet to decrease relative to the oxygen feed level, denoting oxygen conversion.

As can be seen from FIG. 3, catalyst 7, pre-treated with ethylene, acetic acid and nitrogen was the most inhibited, and was more inhibited than a catalyst pre-treated with ethylene and nitrogen alone (catalysts 6 and 9). The nitrogen purge used on catalyst 6 before start-up appeared to make little difference to the inhibition of this catalyst compared to catalyst 9 which had had the same pre-treatment with ethylene and nitrogen, but without the subsequent nitrogen purge.

As comparison of catalyst 7 with catalyst 6 or catalyst 9 demonstrates, exposure to both acetic acid and ethylene inhibits the catalyst to a greater extent than exposure to ethylene alone. However, the catalyst pre-treated with acetic acid and nitrogen only (catalyst 8) showed little or no inhibition compared to a fresh catalyst.

Example 3

A fluidised bed reactor was operated with varying levels of oxygen in the product stream exiting from the reactor. The reactor was operated at a temperature of approximately 155° C., and at a pressure of approximately 7.5 barg. The feed to the reactor comprised ethylene, acetic acid and 3.5mol % oxygen. The oxygen conversion was adjusted to give an oxygen concentration in the reactor exit stream within the range of approximately 0.2 to 2.5 vol %. The oxygen concentration of the reactor exit stream was measured as an average over a 24 hour period prior to taking a sample of the stream for benzene analysis.

Figure 4:
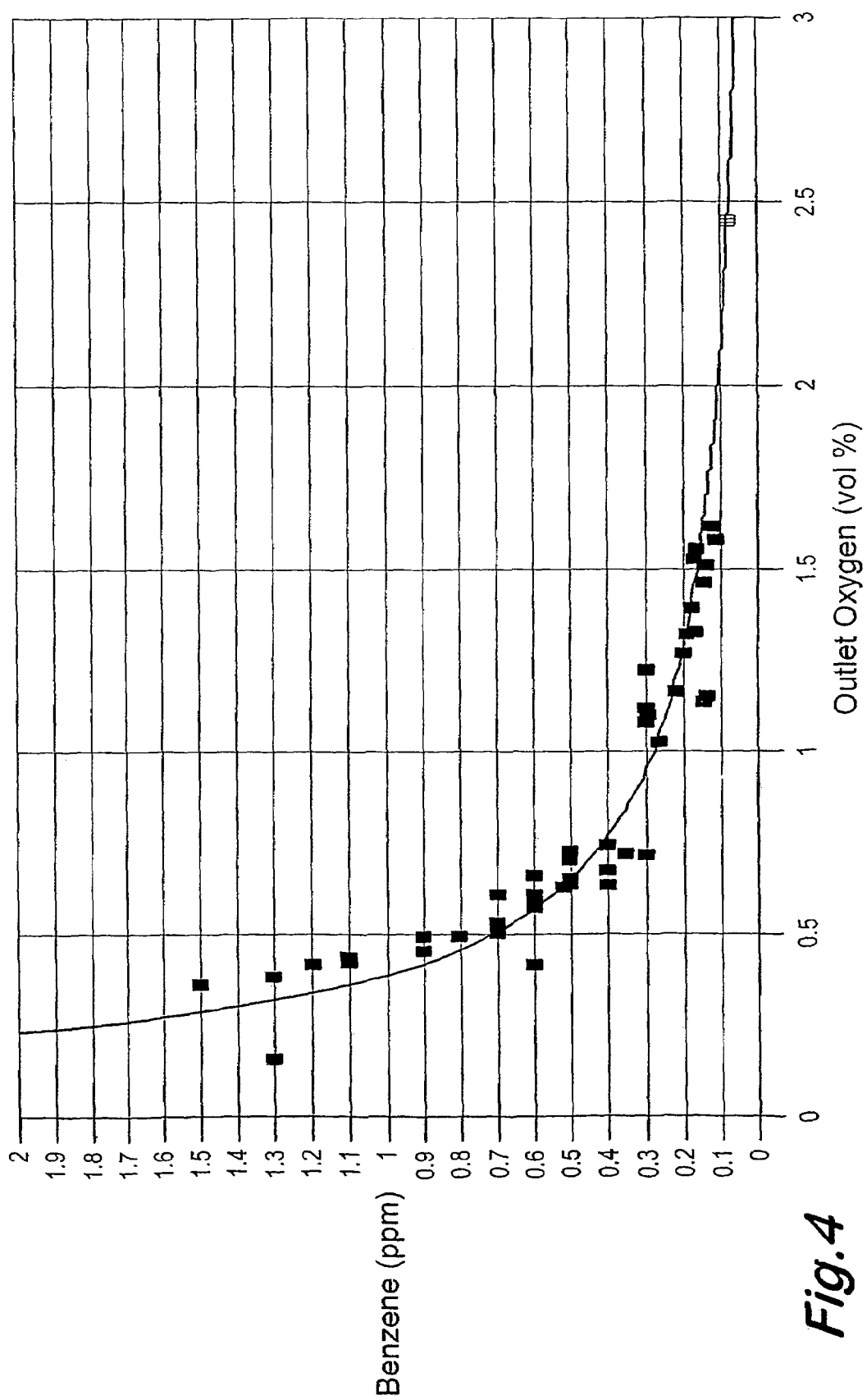
FIG. 4 is a graph showing the increase in benzene production obtained from a fluid bed vinyl acetate process as the oxygen concentration in the product stream from the reaction zone is decreased.

The results are shown in FIG. 4. It can be seen that benzene production increases significantly as the oxygen concentration in the reactor exit stream is reduced. In particular, below about 2 vol % oxygen over 100 ppb of benzene is produced.

The invention claimed is:

1. A fluid bed process for the production of an alkenyl carboxylate comprising reacting an alkene, a carboxylic acid and a molecular oxygen-containing gas in a reaction zone in the presence of a catalyst at an elevated reaction temperature, T, to produce an outlet stream from the reaction zone comprising alkenyl carboxylate and oxygen, wherein during a process upset or shut-down, when the catalyst is contacted with the alkene, at a partial pressure, P, optionally in the presence of the carboxylic acid, and the outlet stream comprises less than 2 vol % oxygen, the partial pressure of the alkene is reduced to at least 50% less than P and/or the reaction temperature is reduced to below 100° C. so as to suppress formation of benzene and/or suppress inhibition of the catalyst, the period of time, Z, during which the catalyst is exposed to the alkene in the presence or absence of the carboxylic acid and at oxygen levels of less than 2 vol % oxygen before the partial pressure of the alkene is reduced to at least 50% less than P and/or the reaction temperature is reduced to below 100° C. being in the range >0 to 12 hours.

2. A process as claimed in claim 1, wherein the catalyst is contacted with alkene and carboxylic acid, and the outlet stream comprises less than 2 vol % oxygen.

3. A process as claimed in claim 1 or claim 2, wherein the outlet stream comprises 0 to 0.5 vol % oxygen.

4. A process as claimed in claim 1 or claim 2, wherein the alkenyl carboxylate product comprises less than 100 ppb benzene.

5. A process as claimed in claim 1 or claim 2, wherein the partial pressure of alkene, P, in the reaction zone is at least 0.3 bar or greater.

6. A process as claimed in claim 1 or claim 2, wherein the partial pressure of alkene in the reaction zone is reduced by removing substantially all the alkene from the reaction zone.

7. A process as claimed in claim 6, wherein the alkene, optional carboxylic acid, and any oxygen present, are removed from the reaction zone by purging the reaction zone with an inert gas.

8. A process as claimed in claim 1 or claim 2, wherein the reaction temperature is reduced to at least 20° C. below T.

9. A process as claimed in claim 1 or claim 2, wherein the catalyst comprises a Group VIII metal, a promoter and optionally a co-promoter.

10. A process according to claim 1, wherein the temperature in the reaction zone, T, is in the range 100° C.-400° C. and the pressure in the reaction zone is from atmospheric pressure up to 20 barg.

11. A process as claimed in claim 3, wherein the outlet stream comprises 0 to 0.2 vol % oxygen.

12. A process as claimed in claim 5, wherein the alkene, P, is ethylene and partial pressure in the reaction zone is at least 1 bar.

13. A process as claimed in claim 12, wherein the partial pressure in the reaction zone is at least 2 bar.

14. A process as claimed in claim 7, wherein the inert gas is nitrogen.

15. A process as claimed in claim 1 or claim 2, wherein the reaction is carried out at a temperature, T, of at least 140° C.

16. A process as claimed in claim 1 or claim 2, wherein the reaction temperature is reduced to 50° C. or lower.

17. A process as claimed in claim 8, wherein the reaction temperature is reduced to at least 50° C. below T.

18. A process as claimed in claim 1 or claim 2, wherein the catalyst is in contact with the alkene, and optionally the carboxylic acid, at low levels of molecular oxygen, for >0 to 6 hours prior to reducing the partial pressure of the alkene and/or reducing the reaction temperature.

19. A process as claimed in claim 1 or claim 2, wherein the catalyst is in contact with the alkene and the carboxylic acid, at low levels of molecular oxygen, for >0 to 6 hours prior to reducing the partial pressure of the alkene and/or reducing the reaction temperature.

* * * * *